US012672880B2

(12) United States Patent
Windheuser et al.

(10) Patent No.: US 12,672,880 B2
(45) Date of Patent: ***Jul. 7, 2026

(54) DEVICE AND METHOD FOR TREATMENT OF HEMORRHOIDS USING SUCTION

(71) Applicant: BOSTON SCIENTIFIC SCIMED, INC., Maple Grove, MN (US)

(72) Inventors: Kevin Windheuser, Hopkinton, MA (US); Oscar R. Carrillo, Jr., Middletown, CT (US); Shaun Dennis Comee, Fiskdale, MA (US); Michael McGOVERN, San Diego, CA (US); Kevin L. Bagley, Natick, MA (US); Nestor Allan Ibanez, Brighton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 36 days.

This patent is subject to a terminal disclaimer.

(21) Appl. No.: 18/819,448

(22) Filed: Aug. 29, 2024

(65) Prior Publication Data

US 2024/0415523 A1    Dec. 19, 2024

Related U.S. Application Data

(63) Continuation of application No. 16/909,660, filed on Jun. 23, 2020, now Pat. No. 12,102,333.
(Continued)

(51) Int. Cl.
*A61B 1/05* (2006.01)
*A61B 17/00* (2006.01)
(Continued)

(52) U.S. Cl.
CPC ............ *A61B 17/1285* (2013.01); *A61B 1/05* (2013.01); *A61B 90/30* (2016.02);
(Continued)

(58) Field of Classification Search
CPC . A61B 1/05; A61B 17/1285; A61B 17/12009; A61B 17/12013;
(Continued)

(56) References Cited

U.S. PATENT DOCUMENTS 9,693,778 B2 * 7/2017 Kamler ............ A61B 17/12009
2014/0058410 A1 * 2/2014 Vermeersch ..... A61B 17/12013
606/140

FOREIGN PATENT DOCUMENTS

CN        201067420 Y * 6/2008

* cited by examiner

*Primary Examiner* — Tan-Uyen T Ho
*Assistant Examiner* — Lindsey R. Rivers
(74) *Attorney, Agent, or Firm* — Fay Kaplun & Marcin, LLP

(57)        ABSTRACT

A device includes a handle having a trigger in combination with a distal portion, the distal portion including a rigid elongated hollow member which receives tissue therein and a plunger fitted with and configured to slide longitudinally within the hollow member to induce suction at a distal end of the hollow member as the plunger is moved proximally within the hollow member. The trigger is hingedly coupled to the plunger so that pulling the trigger slides the plunger proximally with respect to the hollow member to generate suction to draw the tissue into the distal end of the hollow member. The device further includes a tissue treatment mechanism for encircling the tissue received at the distal end of the hollow member.

12 Claims, 5 Drawing Sheets

Related U.S. Application Data

(60) Provisional application No. 62/874,536, filed on Jul. 16, 2019.

(51) Int. Cl.

| | |
|---|---|
| *A61B 17/128* | (2006.01) |
| *A61B 18/00* | (2006.01) |
| *A61B 18/14* | (2006.01) |
| *A61B 90/30* | (2016.01) |
| *A61B 1/00* | (2006.01) |
| *A61B 1/018* | (2006.01) |
| *A61B 1/31* | (2006.01) |
| *A61B 17/12* | (2006.01) |
| *A61B 17/30* | (2006.01) |
| *A61B 17/3205* | (2006.01) |
| *A61B 18/08* | (2006.01) |
| *A61B 90/00* | (2016.01) |

(52) U.S. Cl.
CPC ................. *A61B 2017/0023* (2013.01); *A61B 2017/00407* (2013.01); *A61B 2017/00734* (2013.01); *A61B 2018/00595* (2013.01); *A61B 2018/141* (2013.01)

(58) Field of Classification Search
CPC .. A61B 2017/00407; A61B 2017/0023; A61B 2017/00296; A61B 2017/0042; A61B 2017/00734; A61B 2017/12018; A61B 2017/306; A61B 2017/3452; A61B 2018/141; A61B 90/30
See application file for complete search history.

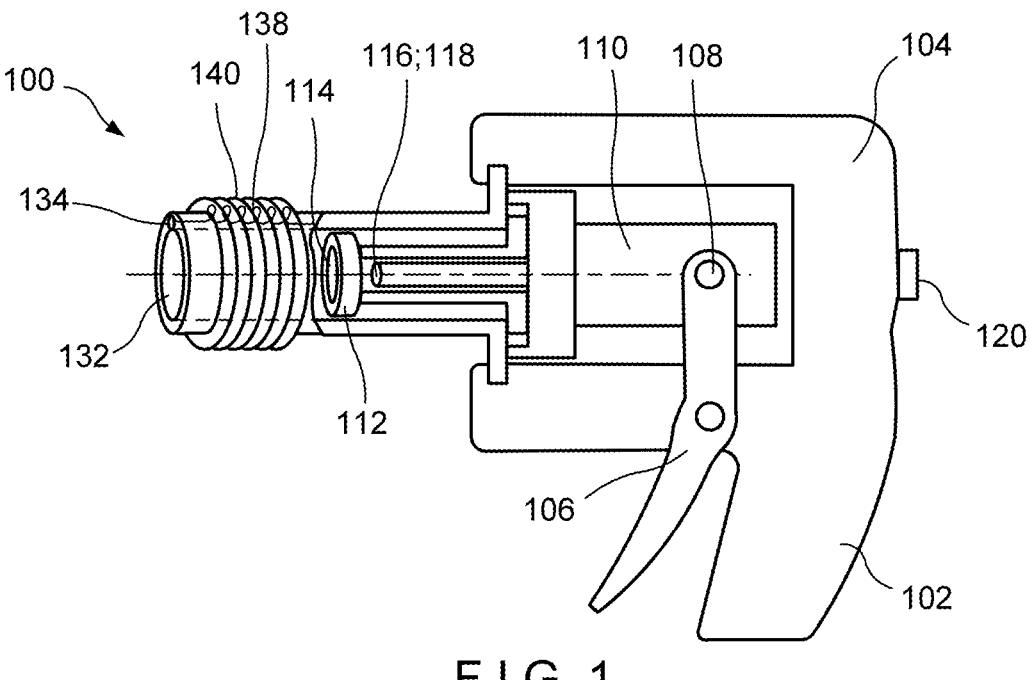
F I G. 1
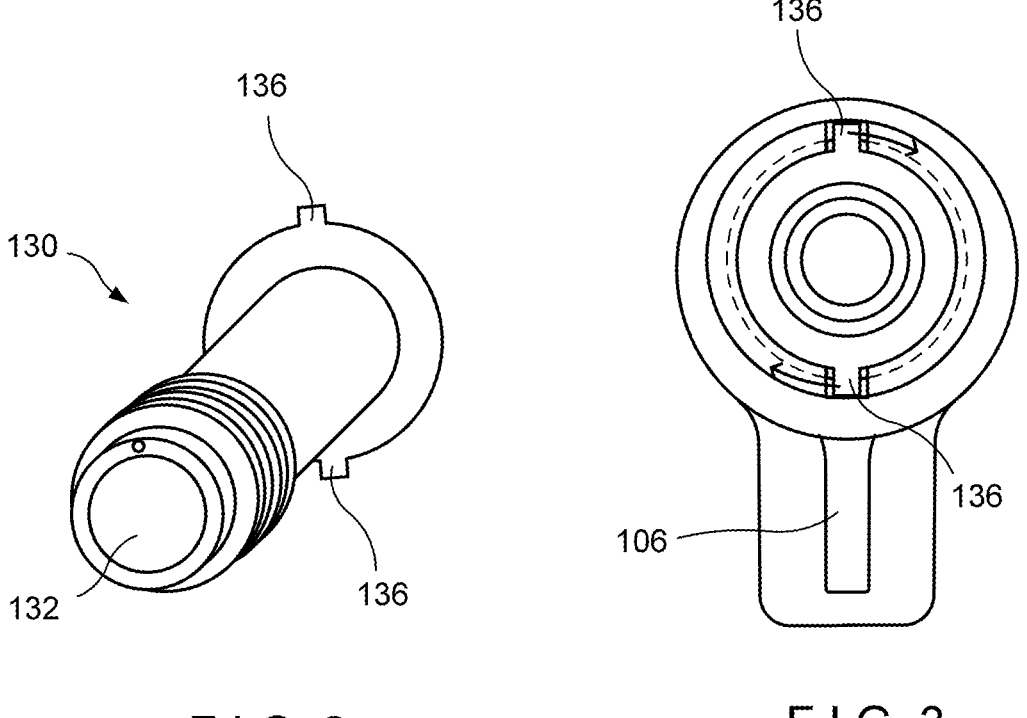
F I G. 2
F I G. 3

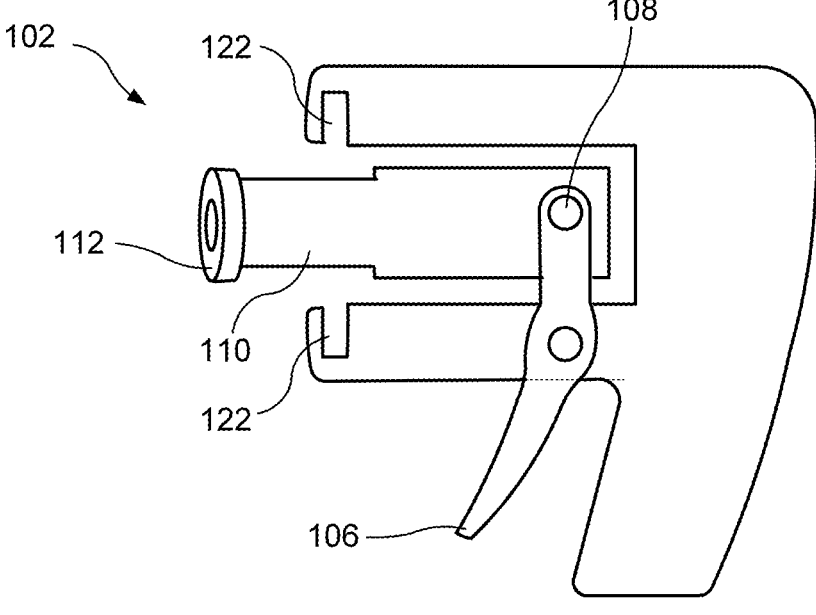
F I G. 4
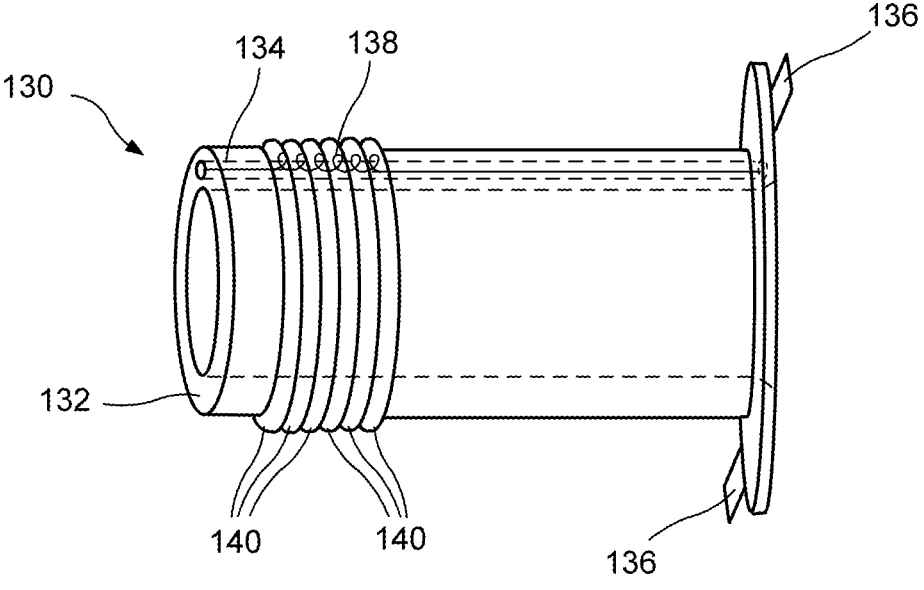
F I G. 5

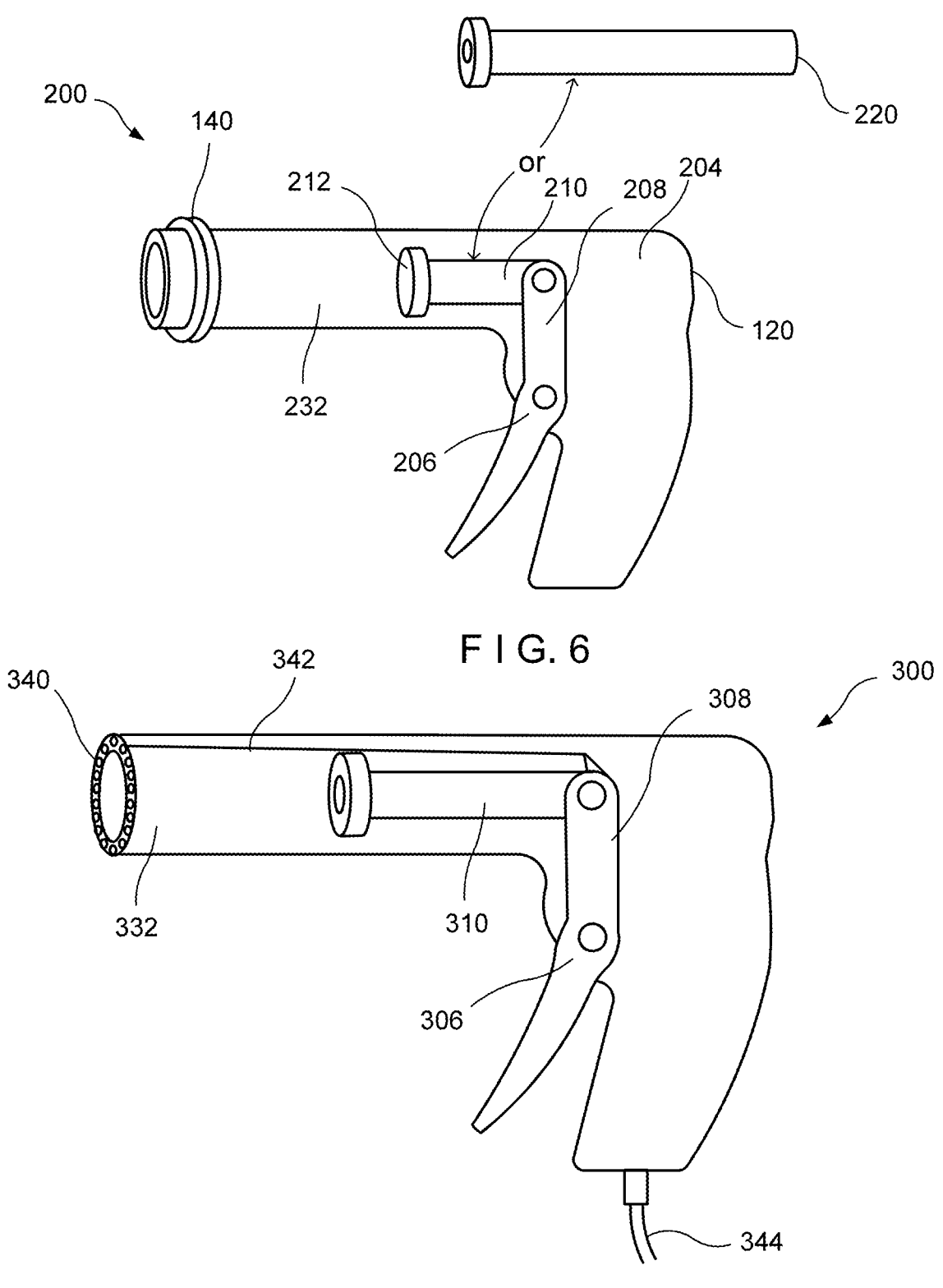
F I G. 6
F I G. 7

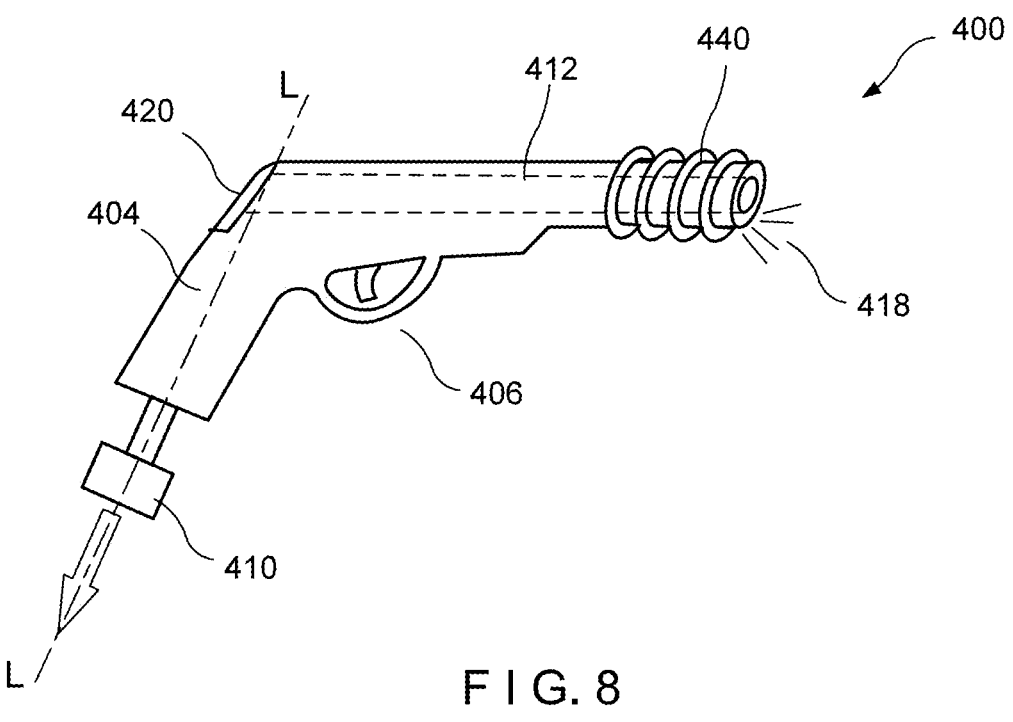
F I G. 8
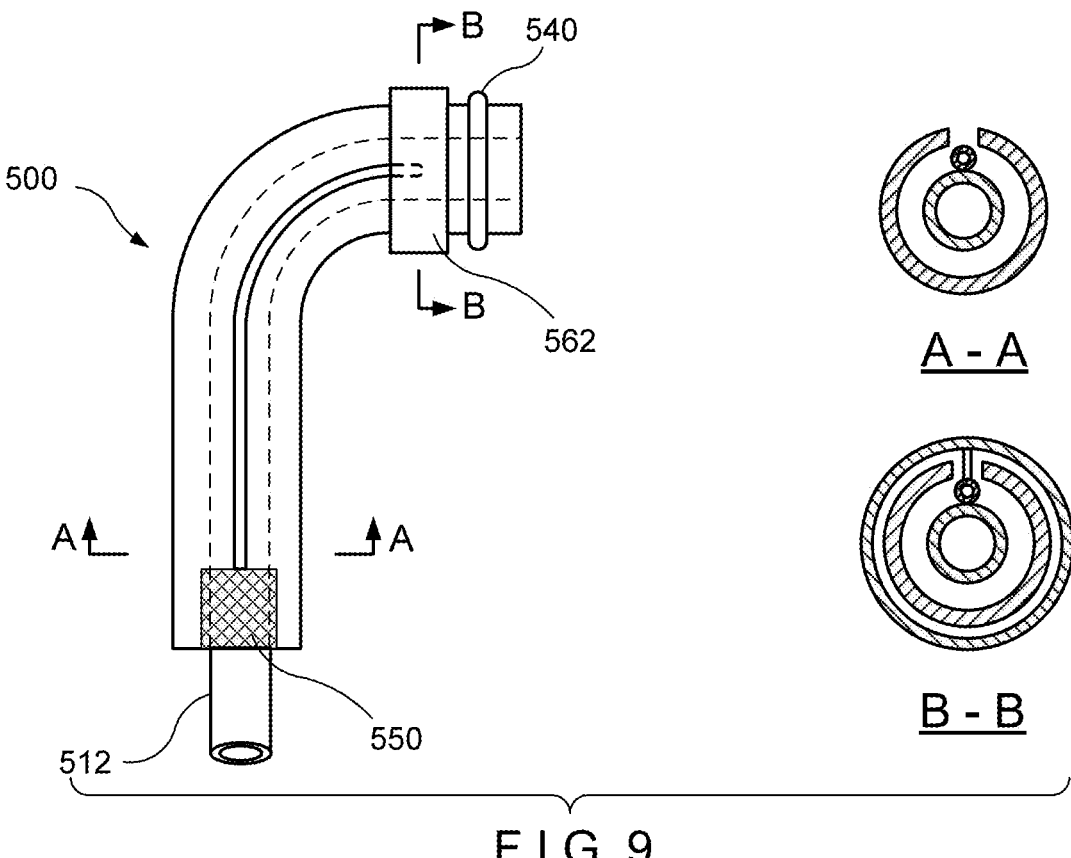
F I G. 9

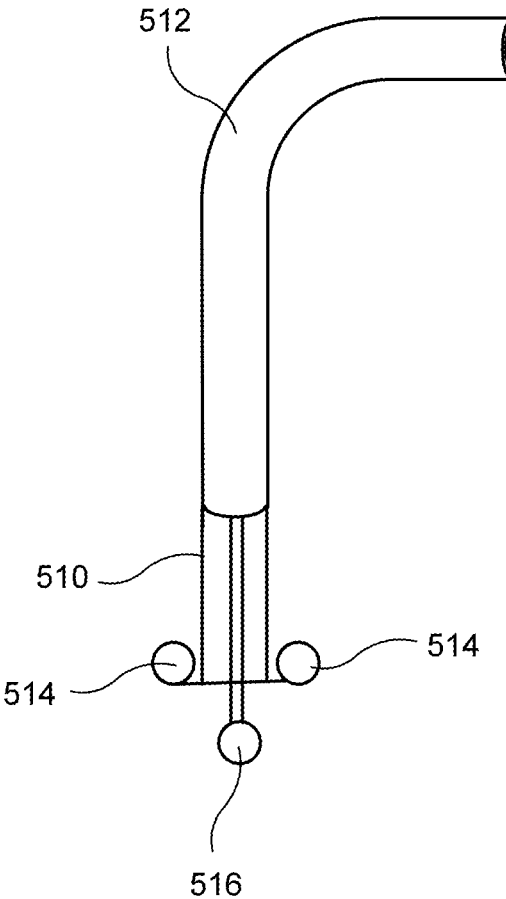
F I G. 10

DEVICE AND METHOD FOR TREATMENT OF HEMORRHOIDS USING SUCTION

PRIORITY CLAIM

The present application is a Continuation of U.S. patent application Ser. No. 16/909,660 filed Jun. 23, 2020, which claims priority to U.S. Provisional Patent Application Ser. No. 62/874,536 filed Jul. 16, 2019; the disclosure of which is incorporated herewith by reference.

FIELD

The present disclosure relates to the treatment of hemorrhoids and, in particular, relates to a device and a method for inducing suction to draw tissue in and further use a treatment mechanism to encircle the tissue.

BACKGROUND

Hemorrhoids are swollen and inflamed veins around the anus or in the lower rectum. Hemorrhoids may be external, forming under the skin around the anus, or internal, forming in the lining of the anus and the lower rectum. Internal hemorrhoids are difficult to visually inspect and treat. It is with the above considerations in mind that the improvements of the present disclosure may be useful.

SUMMARY

The present disclosure relates to a device which includes a handle including a trigger in combination with a distal portion, the distal portion including a rigid elongated hollow member for receiving tissue therein and a plunger fitted with and configured to slide longitudinally within the hollow member to induce suction at a distal end of the hollow member as the plunger is moved proximally within the hollow member. The trigger is hingedly coupled to the plunger so that pulling the trigger slides the plunger proximally with respect to the hollow member to generate suction to draw the tissue into the distal end of the hollow member. The device further comprises a tissue treatment mechanism for encircling the tissue received at the distal end of the hollow member.

An embodiment further comprises, an optical port extending from the handle and an optical lens disposed on a distal surface of the plunger for visualizing an area distal to the device, the optical lens being coupled to the optical port.

An embodiment further comprises, an optical camera for viewing the distal area via the optical lens, wherein the optical camera is coupled to the optical port for attachment to endoscopic equipment.

In an embodiment, the distal portion comprises locking tabs and is attachable to the handle via corresponding locking slots in the handle.

In an embodiment, the distal portion is integrally formed with the handle.

In an embodiment, the tissue treatment mechanism comprises a ligation band deployment mechanism for releasing a ligation band off the distal end of the elongated hollow member to constrict around the tissue received therein.

In an embodiment, the ligation band deployment mechanism comprises a carrier string having a portion extending longitudinally on the exterior of the hollow member and has the ligation band loaded around the hollow member and the string.

In an embodiment, the portion of the carrier string on the exterior of the hollow member is moved distally when the ligation deployment mechanism is actuated, the motion of the carrier string bringing the loaded ligation band to the distal end of the hollow member.

In an embodiment, the ligation deployment mechanism includes one of ratcheting, gears or pulleys for moving the carrier string distally.

In an embodiment, the tissue treatment mechanism comprises a snare mechanism for releasing a snare from the distal end of the elongated hollow member so that the snare severs the tissue received therein.

In an embodiment, the snare is energized.

The present disclosure also relates to a method which includes inserting a distal end of a rigid elongated hollow member of a device into a cavity, the device having a plunger fitted with and configured to slide longitudinally within the hollow member to induce suction at the distal end of the hollow member as the plunger is moved proximally within the hollow member. The method further comprises pulling a trigger hingedly coupled to the plunger so that the plunger slides proximally with respect to the hollow member to generate suction to draw the tissue into the distal end of the hollow member. The method further comprises actuating a tissue treatment mechanism to encircle the tissue received at the distal end of the hollow member.

The present disclosure further relates to a device which includes a hollow housing including a trigger, a viewing port and a rigid elongated distal portion for receiving tissue therein via an open distal end. The device further comprises a plunger disposed at a proximal end of the housing for inducing suction at the open distal end, wherein the viewing port allows visualization distally through the hollow housing and out the distal portion. The trigger actuates a ligation band deployment mechanism for releasing a ligation band off the open distal end to constrict around the received tissue.

Furthermore, the present disclosure relates to a device which includes a rigid hollow elongated member having an open distal end for receiving tissue therein and a plunger disposed at a proximal end of the housing for inducing suction at the open distal end. The device further comprises a slide configured to slide over the exterior of the hollow elongated member and to push a ligation band off the open distal end to constrict around the received tissue.

BRIEF DESCRIPTION

FIG. 1 shows a first device for ligating hemorrhoids according to a first exemplary embodiment of the present disclosure.

FIG. 2 shows a front view of a disposable distal portion of the device of FIG. 1.

FIG. 3 shows a cross-sectional front view of the assembled device of FIG. 1.

FIG. 4 shows a side view of a reusable proximal portion of the device of FIG. 1.

FIG. 5 shows a side view of the disposable distal portion of the device of FIG. 1 with a ligation band loaded thereon.

FIG. 6 shows a second device for ligating hemorrhoids according to a second exemplary embodiment of the present disclosure.

FIG. 7 shows a third device for ligating hemorrhoids according to a third exemplary embodiment of the present disclosure.

FIG. 8 shows a fourth device for ligating hemorrhoids according to a fourth exemplary embodiment of the present disclosure.

FIG. 9 shows a fifth device for ligating hemorrhoids according to a fifth exemplary embodiment of the present disclosure.

FIG. 10 shows a plunger of the device of FIG. 9.

DETAILED DESCRIPTION

The present disclosure may be further understood with reference to the following description and the appended drawings, wherein like elements are referred to with the same reference numerals. Exemplary embodiments of the present disclosure describe partially or wholly disposable devices for treating hemorrhoids. Each of the devices includes a mechanism for drawing a vacuum and receiving a hemorrhoid within a tubular portion of the device. Certain embodiments described herein are ligation devices for applying a ligation band to the base of the hemorrhoid, while other embodiments described herein are snare devices for removing hemorrhoidal tissue. It is noted that the terms proximal and distal, as used herein, are intended to refer to a direction toward (proximal) and away from (distal) a user of the device.

As shown in FIGS. 1-5, a device 100 for ligating hemorrhoids comprises a proximal handle portion 102 including a body 104 supporting a trigger 106. The trigger 106 is coupled to a plunger 110 via a hinged mechanism 108, e.g., a hinge as shown in FIG. 4. Actuation of the trigger causes the hinged mechanism 108 to move the plunger 110 longitudinally (proximally and distally). The proximal portion 102 of this embodiment is a reusable portion configured for attachment to a disposable distal portion 130. The proximal portion 102 has two locking slots 122 sized and shaped to receive corresponding locking tabs 136 extending radially from a disposable distal portion 130. The locking tabs 136 of this embodiment are rectangular (corresponding to rectangular locking slots 122) but may have any different shape for insertion into correspondingly shaped slots 122. The locking tabs 136 engage locking slots 122 by snapping into the slots 122 or by rotating into the slots 122, as shown in FIG. 3. The handle portion 102 further includes a port 120 at the proximal end of the body 104 for attaching electronics and/or viewing equipment such as, e.g., an optical cable or electrical cable connected to a vision system such as, e.g., an endoscopic tower (not pictured) for visualizing the ligation procedure.

The disposable distal portion 130 comprises a hollow tube 132 for receiving a hemorrhoid therein during a ligation procedure. The hollow tube 132 may include a flange at the proximal end having locking tabs 136 extending radially outward for connection with the handle 104. When the disposable distal portion 130 is attached to the reusable proximal portion 102 the plunger 110 resides in the interior of the hollow tube 132 with a proximal end of the plunger 110 attached to the hinged mechanism 108. As would be understood by those skilled in the art, a distal end 112 of the plunger 110 has a cross-section sized and shaped to correspond to the inner diameter of the hollow tube 132 so that, as the plunger 110 moves proximally through the tube 132, suction is created which will draw target tissue into the hollow tube 132. Actuation of the trigger 106 moves the plunger 110 proximally from an initial distal position drawing a partial vacuum within the tube 132 to pull hemorrhoidal tissue into the hollow tube 132. Moving the plunger

110 distally to the distal position releases the vacuum and facilitates separation of the device from surrounding tissue.

The tube 132 is sized to capture the hemorrhoid such that the base of the hemorrhoid is exposed immediately distal to the distal end of the tube 132. The plunger 110 includes an optical lens 114 at the distal end of the plunger 110 facing distally and out the distal end of the tube 132. The plunger 110 of this embodiment includes a camera 116 disposed proximally of the optical lens 114 and connected via suitable wiring to additional components of a vision system via the port 120. The device 100 of this embodiment includes a light source 118 attached to the camera 116. The light source 118 is directed distally to illuminate a target area within the field of view of the camera 116 so that, when the device 100 is directed toward a portion of target tissue within the anal cavity or rectum, the camera 116 provides to the vision system images of the target tissue. The physician may then guide the procedure using the view provided by the camera 116 and the vision system as shown, for example, on a display of an endoscopic tower (not pictured).

A second aspect of the device 100 is a band deployment mechanism for releasing a ligation band 140 from the distal end of the tube 132. Any number of ligation bands 140 may be pre-loaded on the device 100 for deployment in a medical procedure, disposing the bands 140 in an expanded configuration on a distal end of the hollow tube 132. The band deployment mechanism is separate from the hinged mechanism 108 for drawing the plunger 110 proximally and distally within the tube 132. The band deployment mechanism may be any of a variety of mechanisms known in the art. In one embodiment, the band deployment mechanism includes a band carrier string 138 with one or more ligation bands 140 loaded thereon, as shown in FIG. 5. The carrier string 138 of this embodiment extends through a string channel 134 running longitudinally through the wall of the tube 132 and exits the distal end of the channel 134, looping around the distal end of the tube 132 and extending back proximally to engage the ligation bands 140 that are stretched around the outside of the tube 132.

The proximal end of the string 138 may be configured for attachment to the reusable handle portion 102 when the handle portion 102 and the disposable portion 130 are engaged such that the string 138 may be pulled proximally through the channel 134 which, in turn, pulls the portion of the string 138 outside of the tube 132 distally on the exterior of the tube 132 to release one ligation band 140 from the tube 132 to constrict around tissue drawn into the tube 132 as would be understood by those skilled in the art. When the band 140 is released from the tube 132, the band may contract to a reduced diameter, thereby constricting selected tissue.

As those skilled in the art will understand, the string 138 may be wrapped around or may otherwise engage the ligation bands 140 loaded on the tube 132 so that drawing the string 138 proximally pulls the ligation bands 140 distally over the tube 132 so that they may be deployed one-by-one as desired. In an alternate embodiment, the string 138 may have beaded portions that push the ligation bands 140 as the string 138 moves proximally. In either embodiment, the proximal motion of the string 138 eventually brings one or more of the ligation bands 140 to the distal end of the tube 132 and releases the band 140 immediately distal to the tube 132. When hemorrhoidal tissue has been drawn into the tube 132, the release of the band 140 allows the band 140 to constrict around the exposed portion of the tissue as would be understood by those skilled in the art.

The proximal handle portion 102 of the device 100 includes elements of the band deployment mechanism that may be attached to the string 138. In one embodiment, the string 138 is pulled by a ratcheting mechanism that allows for movement of the string 138 only in one direction in controlled increments to deploy the bands 140. In alternate embodiments, the band deployment mechanism may include gears or pulleys. The band deployment mechanism may be actuated by, e.g., a button on the exterior of the handle 102 that draws the string 138 a predetermined distance every time the button is pushed. However, other implementations of an actuator for the band deployment mechanism may be used.

The ligation procedure is performed by first joining the reusable handle portion 102 to the disposable distal portion 130. The string 138 is attached to elements of the band deployment mechanism in the handle 102 prior to the insertion of the locking tabs 136 into the locking slots 122 and locked therein. In a first (unactuated) configuration of the device 100 the plunger 110 is disposed toward the distal end of the hollow tube 132. To advance into a second configuration the trigger 106 is actuated and the hinged mechanism 108 draws the plunger 110 toward the proximal end of the tube 132, creating a partial vacuum. When the device 100 is being used in the ligation procedure and the distal end of the tube 132 has been placed adjacent to a target portion of tissue (e.g., a target hemorrhoid) the vacuum drawn by the trigger stroke draws the hemorrhoid into the tube 132. After the vacuum is pulled, the band deployment mechanism may be initiated to apply a ligation band 140 around the base of the hemorrhoid that has been drawn into the tube 132.

After application of the band 140 the device 100 may return to the first configuration, moving the plunger 110 distally and releasing the suction that permits the banded hemorrhoid to be released from the tube 132. Using the camera 116, the physician may reposition the device 100 adjacent to a second hemorrhoid and draw the plunger 110 proximally (via the trigger 106) to draw the second hemorrhoid into the tube 132. The process may then be repeated to release a second band 140 (the band 140 that was previously positioned immediately proximal of the band that was just released) around the base of the second hemorrhoid. The ligation procedure may be repeated until the ligation bands 140 have all been deployed or until all of the target hemorrhoids have been treated, whereupon the physician may remove the device 100 from the patient. The distal portion 130 may then be detached from the proximal handle portion 102 and disposed of while the proximal portion is sterilized for the next usage.

In a second embodiment, a device 200 for ligating hemorrhoids comprises a housing 204 that serves as a handle and includes a distal hollow tube portion 232, as shown in FIG. 6. The device 200 is a single disposable device with a hinged actuation mechanism 208 coupled to a plunger 210, similar to components of the device 100. The plunger 210 includes a camera and lens configuration similar to that of the device 100, allowing the camera 116 to provide images so that the user may visualize the procedure through the tube 232 via the distal-facing lens 114 and is coupled to endoscopic equipment via the endoscopic port 120. The band deployment mechanism of the device 200 may be similar to that of the device 100. However, the band deployment mechanism of the device 200 may be fabricated without the features of the device 100 allowing for connecting the string 138 with the proximal portion 102. In some embodiments the device 200 may be fabricated as a single piece instead of a disposable portion and a reusable portion connected via locking means.

In an alternate embodiment, the plunger 210 is coupled to an optical viewing port 220 and a camera is not used. The operating physician may visualize the ligation procedure through the viewing port 220 on the proximal end of the device 200. The viewing port 220 is concentric with the plunger 210. In other words, the viewing port 220 extends around the plunger 210 in a cylindrical manner. The hinged mechanism 208 for moving the plunger 210 of this embodiment has a U-shape to avoid covering the viewing axis of the viewing port 220 and the viewing port 220 has slots cut therein to allow the hinged mechanism 208 to move proximally and distally within the viewing port 220. In this way, the plunger 210 is movable within the viewing port 220 and the line of sight from the viewing port 220 out the distal end 212 of the plunger is maintained. The plunger 210 includes the optical lens 114 disposed at the distal end 212 of the plunger 210.

The physician may perform the ligation procedure with the device 200 in a manner substantially similar to that described above for the device 100. The device 200 is advanced from a first configuration to a second configuration to draw a hemorrhoid drawn into the hollow tube 232. When using the alternate embodiment of the device 200, the physician directs the procedure using the viewing port 220 at the proximal end of the device 200. The band deployment mechanism may be any of the aforementioned methods described with respect to device 100. The entirety of the device 200 may be disposed of after the ligation procedure is completed.

In a third embodiment, a snare device 300 is a single disposable device similar to the device 200, comprising, instead of ligation bands, a snare 340, as shown in FIG. 7. The snare 340 is disposed around the distal end of a hollow tube 332 of the snare device 300 and is configured to remove hemorrhoidal tissue by resecting the hemorrhoid at its base, as would be understood by those skilled in the art. Either the camera 116 or alternately an optical viewing port similar to the optical viewing port 220 may be used in the device 300 to allow the physician to direct the snare procedure, in a manner similar to that described in regard to device 200. Accordingly, the plunger 310 operates to draw the hemorrhoid into the tube 332 via the hinged mechanism 308 in a manner substantially similar to the device 200. However, once the hemorrhoid has been drawn into the tube 332 until the base of the hemorrhoid abuts the distal end of the tube 332, the snare 340 is actuated and the hemorrhoid is removed at the portion abutting the distal end of the tube 332.

In an alternate embodiment, the snare 340 may be energized by an active cord 344 coupled to the snare 340 via suitable wiring in the device 300. For example, the device 300 may be operatively coupled to an energy source via active cord 344, for delivering energy to the snare 340. In this manner, a hot snare removes a substantial portion of the hemorrhoid and cauterizes the wound.

The snare 340 may be actuated by the motion of the plunger 310 or may be externally actuated. For example, a cable 342 may connect the snare 340 and the hinged mechanism 308. As the hinge/plunger is drawn back the cable 342 may be drawn, acting to constrict the snare 340. The components may be designed so that the snare 340 is not constricted until the plunger 310 reaches its most proximal position. Alternately, the cable 342 may extend externally to the device 300 and be drawn separately from the plunger 310. When a hot snare is used the snare 340 may be energized when the trigger 306 is actuated. Multiple hemorrhoid treatments are possible without removing the device 300 from the patient anatomy. The snared hemorrhoidal tissue may remain in the tube 332 or may fall out of the device 300, to be removed when the snare procedure is complete.

In a fourth embodiment, a ligation device 400 is a single disposable device comprising a body 404 having a distal tube portion 412 for receiving a hemorrhoid, as shown in FIG. 8, similar to previously described embodiments. However, the device 400 comprises a plunger 410 disposed at a proximal end of the housing 404 configured for manual actuation by the medical professional. The plunger 410 has a handle portion exterior to the device 400 and an interior portion fitted to the interior of the device 400 along a direction of an axis L so that pulling the handle portion proximally along the axis L imposes a partial vacuum on the interior of the device and the distal end of the tube portion 412. The body 404 serves as a handle for the device 400 and comprises a viewing port 420 with a viewing axis extending through the tube portion 412 so that the operating physician may view the ligation procedure. The body 404 has a trigger 406 for actuating a band deployment mechanism and releasing ligation bands 440 loaded on the tube portion 412.

In one embodiment, the band deployment mechanism is similar to the band deployment mechanisms of the previously described devices and includes a carrier string deploying bands as the string is pulled along the exterior of the tube 412. In an alternate embodiment, the band deployment mechanism is a simple tab or lever for disengaging a distal-most band 440 off the distal end of the tube 412. In this alternate embodiment, multiple bands 440 may be pre-loaded onto the device 400, however, after a first band 440 is deployed the remaining bands are manually advanced distally to assume a deployment position.

During the ligation procedure, the physician locates the hemorrhoid via the viewing port 420 using, for example, a power light 418 on the distal end of the tube 412 to illuminate the target tissue. The power light 418 in this embodiment may, for example, be battery powered. Bringing the distal end of the tube 412 adjacent to the hemorrhoid, the physician may manually actuate the plunger 410 (which has a handle remaining exterior to the patient) to impose a vacuum and draw the hemorrhoid into the tube 412. Upon drawing the hemorrhoid into the tube 412, the physician actuates the trigger 406 to apply the ligation band 440 to the hemorrhoid. The physician subsequently releases the vacuum and withdraws the device 400 from the patient. The physician may manually advance a second ligation band 440 to the distal end of the tube 412 and repeat the process to treat any remaining hemorrhoids.

In a fifth embodiment, a ligation device 500 is a single use disposable device comprising a hollow tube 512 with a flexible slide 550 disposed along a substantial portion of the exterior of the tube 512, as shown in FIG. 9. A plunger 510 is disposed at the proximal end of the tube 512, as shown in FIG. 10, for drawing a partial vacuum within the tube to draw target tissue into the tube 512. The plunger 510 may include two finger rings 514 and a thumb ring 516 for the user to draw the target tissue into the tube 512. A pusher 562 on the distal end of the flexible slide 550 is operable to push a ligation band 540 off the distal end of the tube 512 and onto a base of the target tissue that has been drawn into the tube. The proximal end of the slide 550 is manually pushed from the proximal portion of the tube 512, exterior to the patient, and advanced distally along the tube 512, pushing the pusher

562 against the ligation band 540. Once a ligation band has been applied the partial vacuum may be released and the hemorrhoid may be released from the tube 512. The device 500 is manually reloadable with further ligation bands 540 to treat further tissue. The device 500 does not comprise a viewing feature but may be used in conjunction with an anoscope to visualize the procedure. Cross-Section A-A of FIG. 9 depicts a cross-section of the proximal end of the flexible slide 550 while Cross-Section B-B of FIG. 9 depicts a cross-section of the distal end of the flexible slide 550.

It will be appreciated by those skilled in the art that changes may be made to the embodiments described above without departing from the inventive concept thereof. It should further be appreciated that structural features and methods associated with one of the embodiments can be incorporated into other embodiments. It is understood, therefore, that this invention is not limited to the particular embodiment disclosed, but rather modifications are also covered within the scope of the present invention as defined by the appended claims. Combinations of the above embodiments, and other embodiments not specifically described herein will be apparent to those of skill in the art upon reviewing the above description. Thus, the scope of various embodiments includes any other applications in which the above compositions, structures, and methods are used.

Some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

As used herein, the singular forms "a," "an," and "the" are intended to include the plural forms as well, unless the context clearly indicates otherwise. It will be further understood that the terms, "comprises" and/or "comprising," or "includes" and/or "including" when used herein, specify the presence of stated features, regions, steps elements and/or components, but do not preclude the presence or addition of one or more other features, regions, integers, steps, operations, elements, components and/or groups thereof.

Furthermore, the terms "substantial" or "substantially," as well as the terms "approximate" or "approximately," can be used interchangeably in some embodiments, and can be described using any relative measures acceptable by one of skill. For example, these terms can serve as a comparison to a reference parameter, to indicate a deviation that will still provide the intended function. Although non-limiting, the deviation from the reference parameter can be, for example, in an amount of less than 1%, less than 3%, less than 5%, less than 10%, less than 15%, less than 20%, and so on.

The invention claimed is:

1. A device, comprising:
   a handle portion including a body supporting a trigger;
   a hollow member extending distally from the handle portion, the hollow member having an open distal end configured to receive tissue therein and a plunger configured to slide longitudinally within the hollow member to induce suction through the open distal end of the hollow member as the plunger is moved proximally within the hollow member, the trigger being hingedly coupled to the plunger so that pulling the trigger slides the plunger proximally within the hollow member to generate suction to draw the tissue into the open distal end of the hollow member;

a tissue ligating member encircling the open distal end of the hollow member;

a release mechanism configured to release the tissue ligating member from the open distal end of the hollow member when tissue has been drawn into the open distal end of the hollow member;

an optical port at a proximal end of the body; and an optical lens disposed on a distal surface of the plunger configured to visualize a distal area which is distal to the device, the optical lens being coupled to the optical port.

2. The device of claim 1, further comprising:

an optical camera for viewing the distal area via the optical lens, wherein the optical camera is coupled to the optical port configured to be attached to endoscopic equipment.

3. The device of claim 1, wherein the handle portion comprises locking tabs and is attachable to the hollow member via corresponding locking slots in the body of the handle portion.

4. The device of claim 1, wherein the hollow member is integrally formed with the handle portion.

5. The device of claim 1, wherein the release mechanism comprises a ligation band deployment mechanism which is configured to release the tissue ligating member off the open distal end of the hollow member to constrict around the tissue received therein.

6. The device of claim 5, wherein the ligation band deployment mechanism comprises a carrier string having a portion extending longitudinally on an exterior of the hollow member to couple to the tissue ligating member.

7. The device of claim 6, wherein the portion of the carrier string on the exterior of the hollow member is moved distally when the ligation band deployment mechanism is actuated, a motion of the carrier string bringing the loaded ligation band to the open distal end of the hollow member.

8. The device of claim 7, wherein the ligation band deployment mechanism includes one of a ratchet, gears or pulleys for moving the carrier string distally.

9. The device of claim 5, further comprising:

a ligation band receiving surface proximal to the open distal end of the hollow member configured to receive a plurality of ligation bands thereover in a stretched state so that, when one of the ligation bands is released off the open distal end of the hollow member, the ligation band constricts around tissue received in the hollow member.

10. The device of claim 1, wherein the hollow member is couplable to the handle portion via a plurality of locking tabs extending from a flange of the hollow member so that the hollow member is configured to be separated from the handle portion.

11. The device of claim 1, wherein the tissue ligating member is a snare and the release mechanism includes a snare release mechanism configured to release the snare.

12. The device of claim 11, wherein the snare is is configured to be coupled to an energy source.

* * * * *